United States Patent [19]

Nichol et al.

[11] Patent Number: 4,587,340

[45] Date of Patent: May 6, 1986

[54] BIOPTERIN ANALOGS

[75] Inventors: Charles A. Nichol; John F. Reinhard, Jr., both of Durham; Gary K. Smith, Raleigh; Eric C. Bigham, Chapel Hill, all of N.C.

[73] Assignee: Burroughs Wellcome Co., Research Triangle Park, N.C.

[21] Appl. No.: 620,152

[22] Filed: Jun. 13, 1984

Related U.S. Application Data

[63] Continuation-in-part of Ser. No. 533,786, Sep. 19, 1983, abandoned.

[51] Int. Cl.$^4$ ............... C07D 475/04; A61K 31/505
[52] U.S. Cl. .............................. 544/258; 544/33 G
[58] Field of Search ..................... 544/258; 424/251

[56] References Cited

U.S. PATENT DOCUMENTS 4,094,874  6/1978  Catalucci ........................ 544/258
4,156,725  5/1979  Wood ............................. 424/251

Primary Examiner—Donald G. Daus
Assistant Examiner—Robert Benson
Attorney, Agent, or Firm—Donald Brown

[57] ABSTRACT

This invention provides the intermediates of formula II-A below, useful to make the pterin compounds of formula I below. The pterin compounds are used in human and veterinary medicine.

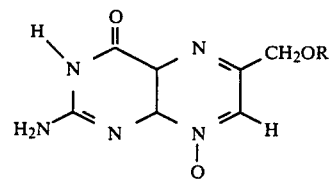

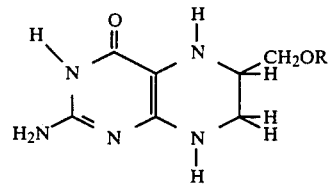

wherein R represents a lower alkyl of 1 to 8 carbons.

3 Claims, No Drawings

BIOPTERIN ANALOGS

This application is a continuation-in-part of application Ser. No. 553,786, filed Sept. 19, 1983, now abandoned.

The present invention relates to a series of pteridines known as pterins which are analogs of tetrahydrobiopterin, to pharmaceutical formulations containing them, to processes for their preparation and to the use thereof in human medicine. More specifically the invention relates to certain biopterin analogs and their use in the treatment of Parkinsonism (and other diseases caused by a deficiency of biogenicamines (e.g., catecholamines and serotonin) in the brain and the perpheral nervous system) and the tetrahydrobiopterin-deficient phenylketonurias (atypical PKU).

The invention accordingly provides the pterin compounds of formula (I) and their use in human and veterinary medicine.

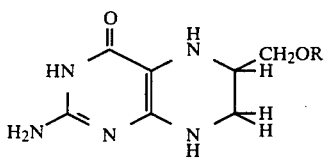

wherein R represents a lower alkyl group (straight or branched) of 1-8 carbons (for this formula and all other formulas herein) including all stereo isomers thereof or a pharmaceutically acceptable salt thereof.

Most preferred of the compounds of formula (I) are (+−)-2-amino-5,6,7,8-tetrahydro-6-ethoxymethyl-4(3H)-pteridinone, (+−)-2-amino-5,6,7,8-tetra-hydro-6-methoxymethyl-4(3H)-pteridinone, (+−)-2-amino-5,6,7,8-tetrahydro-6-n-propoxymethyl-4(3H)-pteridinone and (+−)-2-amino-5,6,7,8-tetrahydro-6-n-butoxymethyl-4-(3H)-pteridinone or pharmaceutically acceptable salts thereof. It is generally accepted that certain substances known as neurotransmitters are required at the microscopic regions, known as synapses, between nerve cells (neurons) to transmit the nerve impulses throughout the body.

Over thirty substances are known or suspected to be neurotransmitters and each has a characteristic excitatory or inhibitory effect on neurons. Excesses or deficiencies of these transmitters can be manifested as moderate to severe neurological or mental disorders. While neurons are present throughout the body, imbalances of neurotransmitters at synapses of the neurons in the brain are by far the most critical and produce the most pronounced effects.

Of the numerous neurotransmitters known or thought to be operating at synapses, a smaller group collectively known as biogenic amines have received the most study. Particularly important members of this group are the catecholamines such as dopamine and norepinephrine (noradrenaline) and the indole amine, serotonin.

Tetrahydrobiopterin ($BH_4$) is an essential cofactor for the rate limiting enzymes of biogenic amine synthesis, tyrosine and tryptophan hydroxylases, and for the liver enzyme which converts phenylalanine to tyrosine (Kaufman, S. and Fisher, D. B., *Molecular Mechanisms of Oxygen Activation*, Hayaishi, O. Ed., Acad. Press, N.Y. (1974)).

Knowledge of the chemical pathology of neurological disorders has expanded tremendously during the last two decades. For example, neurological disorders have been described whose symptoms can be associated with decreases in the number of catecholamine and/or serotonin molecules released at certain synaptic sites. As a category, they may be thought of an 'catecholamine-deficiency disorders'. One example is Parkinson's disease (also known as Parkinsonism), where a deficiency in brain dopamine has been linked with the symptoms of rigidity, tremor and akinesia. Another example is chronic preganglionic autonomic insufficiency known as the Shy-Dagger syndrome which is associated with both peripheral sympathetic dysfunction and a degeneration of brain neurons in the basal ganglia. The peripheral sympathetic dysfunction most likely reflects a loss of formation and release of the pressor catecholamine norepinephrine, while the rigidity and alkinesia most likely reflects a loss of the capacity to form dopamine in certain brain regions.

In all of these cases the catecholamines, whose levels are diminished, are formed through the action of tyrosine hydroxylase which is rate-limiting for their formation. This enzyme requires tyrosine, oxygen and a reduced pterin cofactor, tetrahydrobiopterin ($BF_4$), for activity. While oxygen and tyrosine are not normally limiting for tyrosine hydroxylase, the levels of $BH_4$ may normally be well below the levels required to saturate this enzyme. In fact, there are reports in the scientific literature indicating the levels of this cofactor are severely diminished in Parkinson's disease and in the Shy-Drager syndrome (Nagatsu, T., *Neurochem. Intern.*, 5, 27 (1983)). Logically, the rate of dopamine biosynthesis would be increased by reversing this deficit. Administration of $BH_4$ has been shown to nearly double striatal dopamine synthesis, as well as noradrenaline synthesis in peripheral nerves (Nagatsu, vide supra also Cloutier, G. and Weiner, N., *J. Pharm. Exp. Ther.*, 186, 75 (1973)). In fact, $BH_4$ administration has been reported to improve the symptoms of Parkinson's disease (Narabayashi, H., Kondo, T., Nagatsu, T., Sugimoto, T. and Matsurra, S., *Proc. Japan Acad.*, 58, Ser. B, 283 (1982)). A group of physchiatric disorders known as endogenous depression may also involve reduced neuronal formation of catecholamines and serotonin. In fact, $BH_4$ has recently been shown to improve the symptoms of depression in several patients (Curtius, H., Müldner, H. and Niederwieser, A., *J. Neurol. Transmission*, 55, 301 (1982)). This natural cofactor is however, expensive, unstable, and it penetrates brain poorly. Thus, treatment with $BH_4$ is not the treatment of choice. Previously known synthetic cofactor replacements for $BH_4$ all cause tyrosine hydroxylase (TH) to bind its substrate tyrosine more weakly. Thus, the administration of these previously known synthetic cofactors for the acceleration of dopamine biosynthesis in the treatment of catecholamine deficiency causes TH to become unsaturated with tyrosine.

The compounds of formula (I), quite unexpectedly, do not decrease the binding of tyrosine to tyrosine hydroxylase and do promote dopamine formation by this enzyme at rates equal to that observed with the natural cofactor, $BH_4$. Further, the compounds of formula (I) enter the brain more easily than $BH_4$ and accelerate dopamine biosynthesis better than the natural cofactor when administered peripherally (orally). Thus, the administration of compounds of formula (I) for catecholamine deficiency accelerate dopamine biosynthesis without coadministration of exogenous tyrosine. An additional surprising property of the compounds of formula (I) is selectivity for tyrosine hydroxylase when the carbon chain length of R is greater than two carbons. The compound of formula (I) wherein R=$C_2H_5$ is active for tyrosine, tryptophan and phenylalanine hydroxylases, whereas the compounds of formula (I) where in R=$C_3H_7$, $C_4H_9$ and $C_8H_{17}$ are successively less active for tryptophan and phenylalanine hydroxylases. The greatest specificity for tyrosine hydroxylase among these compounds is found in that wherein R=$C_4H_9$.

Endogenous (psychotic) depression is thought to involve decreased levels of serotonin and noradrenaline at brain synapses. The compounds of formula (I) function as cofactors for tyrosine and tryptophan hydroxylases. Thus, these compounds will ameliorate the symptoms of endogenous depression by promoting the synthesis of both catecholamines and serotonin in the brain.

In addition to actions on the central nervous system, the compounds of formula (I) can replace $BH_4$ in the liver and promote the hydroxylation of phenylalanine. Indeed, a small percentage of all patients with phenylketonuria suffer from a tetrahydrobiopterin-deficient form of phenylketonuria. This "atypical PKU" has been successfully treated with large quantities of $BH_4$ (Nagatsu, vide supra). Since the compounds of formula (I) are more lipophilic and have better bioavailability than $BH_4$, considerably smaller doses could be used to treat this atypical PKU. The compounds of formula (I) have at least 2 benefits. First, they act as cofactors for hepatic phenylalanine hydroxylase to reduce plasma phenylalanine levels. Second, they will act within the brain as cofactors for tyrosine and tryptophan hydroxylase, to correct the $BH_4$ deficient reductions in cerebral catecholamine and serotonin levels which are also seen in atypical PKU. Paradoxically, large amounts of phenylalanine inhibit phenylalanine hydroxylase with $BH_4$ as cofactor. In contrast, the compounds of formula (I) do not show this substrate inhibition and would remain effective in the presence of large circulating levels of phenylalanine.

Tetrahydropterins, upon reacting with tyrosine, tryptophan or phenylalanine hydroxylase, give rise to an unstable quininoid intermediate which is reduced back to the tetrahydro form by dihydropteridine reductase (DHPR). The compounds of formula (I) are recycled by DHPR at rates three times faster than that of the natural cofactor. This feature would extend the useful biologic life of these compounds, resulting in a favorable duration of action.

Tetrahydropterins, after enzymatic or chemical oxidation with molecular oxygen can also rapidly form the 7,8-dihydropterin structure which is not reducible by DHPR. Dihydrofolate reductase (DHFR) will reduce certain 7,8-dihydropterins to the corresponding tetrahydropterins. 7,8-Dihydrobiopterin (7,8-$BH_2$) can be reduced at a rate 2.5% that of dihydrofolate, the natural substrate. Previously known TH cofactor analogs are reduced at rates even slower than 7,8-$BH_2$ which shortens their lifetime in vivo. Surprisingly the dihydropterins derived from compounds of formula (I) are reduced by DHFR at rates 8 times, and more, faster than $BH_2$. Thus, DHFR increases the effective in vivo lifetime of compounds of formula (I) which improves their efficacy.

Compounds of formula (I) and their salts may be synthesized by methods known in the art of synthesis of compounds having analogous structures. In compounds of formula (IIA), (III), (V) and (VI) n=0 or 1.

A method of preparing compounds of formula (I) comprises reacting a compound of formula (IIA) with a reducing agent capable of donating hydrogens such as $H_2$/catalyst, sodium cyanoborohydride or sodium borohydride all in a suitable solvent under conditions normally used for these reagents. Compounds of formula (I) may also be prepared by reduction of compounds of formula (IIB), the 7,8-$BH_2$ compounds (vide supra), in vitro or in vivo with a suitable enzymatic reagent such as dihydrofolate reductase.

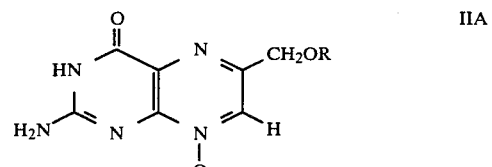

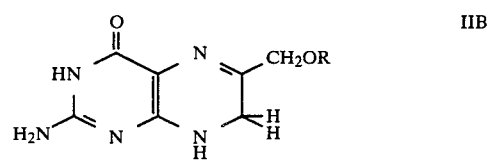

Compounds of formula (II) may be prepared by hydrolysis of a compound of formula (III) with a suitable agent such as an aqueous sodium hydroxide solution.

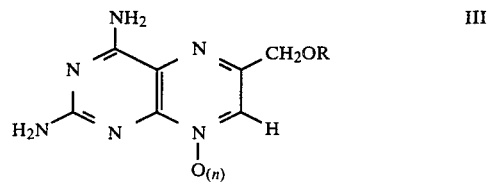

In turn, compounds of formula (III) may be prepared by condensation of the compound of formula (IV) with compounds of formula (V) in the presence of a base, such as sodium alkoxide, in an alcohol under conditions similar to those described in Taylor, et al., *J. Org. Chem.*, 2817, 38 (1973). A specific example is sodium methoxide in methanol.

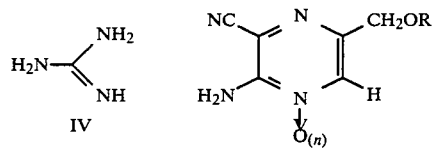

Compounds of formula (V) may be prepared by refluxing a compound of formula (VI) in an alcohol of formula (VII).

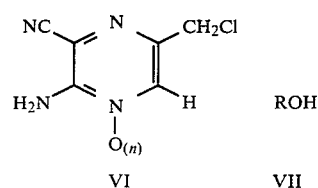

Compounds of this invention may be used to treat Parkinson's disease, endogenous depression, orthostatic hypotension, muscular dystonia and other disorders which arise from deficiencies of catecholamines and serotonin at the pre-synaptic sites of neuronal junctions. These compounds may also be used to treat the $BH_4$-deficient phenylketonurias (atypical PKU).

The amount of the active compound, i.e. a compound of formula (I), required for use in the above disorder will, of course, vary with the route of administration, the condition being treated, and the person undergoing treatment, but is ultimately at the discretion of the physician. However, a suitable dose for treating these disorders is in the range of from 0.5 to 20 mg per kilogram body weight per day preferably from 1 to 10 mg/kg body weight per day, most preferably from 2 to 7 mg/kg body weight per day, a typical preferred dose is 5 mg/kg body weight per day.

The desired dose is preferably presented as between one and four subdoses administered at appropriate intervals throughout the day. Thus where three sub-doses are employed each will lie in the range of from 0.17 to 6.7 mg/kg body weight; a typical dose from a human recipient being 1.7 mg/kg body weight.

If desirable, the catecholamine and serotonin precursors l-tyrosine or l-tryptophan may be administered concurrently with a compound of formula (I) at the rate of 25 mg/kg to 1000 mg/kg body weight. These amino acids may be given in the same pharmaceutical formulation, e.g., tablet or capsule, as a compound of formula (I) or in a separate pharmaceutical formulation.

While it is possible for the active compound or compounds to be administered alone as the raw chemicals, it is preferable to present the active compound or compounds as pharmaceutical formulations. Formulations of the present invention comprise a compound of formula (I) together with one or more pharmaceutically acceptable carriers thereof and optionally any other active therapeutic ingredients.

The carrier(s) must be pharmaceutically acceptable in the sense of being compatible with the other ingredients of the formulation and not deleterious to the recipient thereof. The carrier may contain a preservative agent such as ascorbic acid.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a finely divided solid carrier and then, if necessary, shaping the product into the desired formulations or packaging in a suitable container.

Formulations of the present invention suitable for oral administration may be presented as discrete units such as capsules, cachets, tablets or lozenges, each containing a predetermined amount of the active compound(s); as a powder or granules; or a suspension in a non-aqueous liquid such as a syrup, an elixir, an emulsion or a draught. The active compound(s) may also be presented as a bolus or depot formulation.

A tablet may be made by compression or molding, optionally with one or more accessory ingredients. Compressed tablets may be prepared by compressing in a suitable machine, the active compound being in a free-flowing form such as a powder or granules, optionally mixed with a binder, lubricant, inert diluent, surface active or dispersing agent. Molded tablets may be made by molding in a suitable machine, comprising a mixture of the powdered active compound(s) with any suitable carrier.

Formulations for rectal administration may be presented as a suppository with a usual carrier such as cocoa butter.

Formulations suitable for parenteral administration can be made sterile and packed as dry solids in sealed sterile nitrogen-purged containers. At the time of parenteral administration a specified amount of sterile water is added to the drug formulation and the resulting solution is administered to the patient with a minimum of delay since the compounds of formula (I) tend to be unstable in aqueous solution over a period of time.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

Compounds of the formula (I) are particularly useful in increasing the synthesis of tyrosine, dopamine, norepinephrine and serotonin in mammals such as rats and humans. Such effects are produced by administration preferably orally or parenterally.

The following examples are provided by the way of illustration of the present invention and should in no way be construed as a limitation thereof.

EXAMPLE 1

(+ −)-2-Amino-5,6,7,8-tetrahydro-6-methoxymethyl-4(3H)-pteridinone

2-Amino-3-cyano-5-chloromethyl pyrazine (0.95 g) was reacted with a large excess of dry methanol, under nitrogen, at reflux, for about 18 hours. The resulting reaction mixture was filtered and the filtrate was taken to dryness by evaporation. A yellow residue was collected and extracted twice with boiling methylene chloride. These extracts were filtered and the solvent evaporated to give 2-amino-3-cyano-5-methoxymethylpyrazine which was then treated with an excess of guanidine in methanol according to the method of Taylor (*J. Org. Chem.*, 2817, 38, (1973)). Most of the product of this reaction precipitated and was collected by filtration. The filtrate was mixed with silica gel, stripped of solvent by evaporation, and the residue was placed on a silica gel column. This column was eluted with methanol (5%) in ethylacetate to yield a second crop of product which was added to that previously collected. The combined crops were recrystallized from methanol to yield 2,4-diamino-6-methoxymethyl pteridine (mp 248°–251°).

The diaminopteridine, vide supra, was hydrolyzed in 1N NaOH at 70° C. for 3 hr. The resulting basic solution was then acidified with acetic acid, and the yellow product was filtered, washed with 95% ethanol and ethyl ether, and dried under vacuum overnight to yield 0.5 g (83%) of 2-amino-6-methoxymethyl-4(3H)-pteridinone as a yellow powder: UV (0.1N NaOH) $\lambda_{max}$ 255 nm (22300), 277.5 nm sh (6200), 364 nm (7100); NMR: δ ($d_6$-DMSO) 3.36 (s, OMe); 4.53 (s, $CH_2O$); 7.32 (br s, $NH_2$); and 8.63 (s, 7-H). Anal. calcd. for $C_8H_9N_5O_2.7/10H_2O$: C, 43.72; H, 4.77; N, 31.86. Found: C, 43.77; H, 4.77; N, 31.63.

The pteridinone (0.5 g, $2.4 \times 10^{-3}$ mol) previously prepared, vide supra, was hydrogenated under 1 atm of $H_2$ in 30 mL of distilled trifluoroacetic acid over 0.02 g of $PtO_2$ for an hour. The mixture was diluted with 25 mL of 6N HCl, filtered, and evaporated. The crude product, the tetrahydro compound, was recrystallized twice from 6N HCl/acetonitrile to give 2-amino-5,6,7,8-tetrahydro-6-methoxymethyl-4(3H)-pteridinone as a light brown solid (0.6 g, 85%): UV: (0.1N HCl) $\lambda_{max}$ 215.5 nm (19800), 264 nm (19900); IR: (KBr) 3300, 1665, 1570, 1540, 1470, 1365, 1300, 1150, 1110, 1005, 955, and 750 cm$^{-1}$; NMR: δ ($d_6$-DMSO) 3.29 (s,OMe); 3.4(m, CH's); 3.6 (br s, OCH$_2$); 8.0 (NH). Anal. calcd. for $C_8H_{13}N_5O_2.2HCl.\frac{1}{2}H_2O$: C, 32.78; H, 5.50; N, 23.89; Cl, 24.19. Found: C, 32.75; H, 5.54; N, 23.80; Cl, 24.21.

EXAMPLE 2

(+ −)-2-Amino-5,6,7,8-tetrahydro-6-n-butoxymethyl-4(3H)-pteridinone

This compound was made in a manner similar to that of the 6-methoxymethyl title compound described in Example 1 (vide supra) except for the two following major exceptions: the n-butoxymethylpyrazine was made by heating the chloromethylpyrazine (VI) in n-butanol instead of methanol, and the guanidine reaction was carried out in heated n-butanol instead of refluxing methanol.

Spectra and microanalytical data of the three intermediates and final product are the following:

2A. 2-Amino-3-cyano-5-n-butoxymethylpyrazine. NMR: δ ($d_6$-DMSO) 0.89 (t, 3H); 1.1-1.8 (m, 4H); 3.43 (t, 2H); 4.35 (s, 2H); 7.22 (br s, 2H); 8.25 (s, 1H). IR: (CHCl$_3$) 3694, 3526, 3414, 2930, 2866, 2220 (CN), 1723, 1612, 1463, 1377, 1275, 1088 cm$^{-1}$.

2B. 2,4-Diamino-6-n-butoxymethylpteridine. mp 237°-238° C. dec; NMR: δ ($d_6$-DMSO) 0.87 (t, 3H); 1.0-1.7 (m, 4H); 3.51 (t, 2H); 4.58 (s, 2H); 6.63 (br s, 2H); 7.59 (br s, 2H); 8.73 (s, 1H). Anal. Calcd. for $C_{11}H_{16}N_6O$: C, 53.21; H, 6.50; N, 33.85. Found: C, 53.02; H, 6.51; N, 33.75.

2C. 2-Amino-6-n-butoxymethyl-4(3H)-pteridinone. mp >300°, UV: (0.1N NaOH) $\lambda_{max}$ 256 (27,400), 276.5 sh (11,300), 364.5 (7,200) nm. NMR: δ ($d_6$-DMSO) 0.87 (t, 3H); 1.0-1.8 (m, 4H); 3.50 (t, 2H); 4.57 (s, 2H); 6.97 (br s, 2H); 8.67 (s, 1H) (ring NH exchanged out due to large amount of $H_2O$ present). Anal. calcd. for $C_{11}H_{15}N_5O_2$. 0.3$H_2O$: C, 51.87; H, 6.17; N, 27.50. Found: C, 51.80; H, 6.17; N, 27.55.

2D. (±)-2-Amino-5,6,7,8-tetrahydro-6-n-butoxymethyl-4(3H)-pteridinone. mp 211°-212° (dec). UV: (0.1N HCl) $\lambda_{max}$ 265 (15,800) nm. NMR: δ ($d_6$-DMSO) 0.88 (t, 3H); 1.0-1.7 (m, 4H); 3.0-3.8 (m, 7H); 4.95, 6.85, 7.45, 10.5 (br humps). Anal. Calcd. for $C_{11}H_{19}N_5O_2$.1.75HCl.$H_2O$: C, 39.42; H, 6.84; N, 20.90; Cl, 18.52. Found: C, 39.40; H, 6.74; N, 21.06; Cl, 18.61.

EXAMPLE 3

(+ −)-2-Amino-5,6,7,8-tetrahydro-6-methoxymethyl-4(3H)-pteridinone 3A. 2-Amino-6-methoxymethyl-4(3H)-pteridinone-8-oxide. 2,4-Diamino-6-methoxymethylpteridine-8-oxide (E. C. Taylor and T. Kobayashi, J. Org. Chem., 2817, 38, (1973)) was treated with sodium hydroxide in a manner analogous to that described in Example 1 to give the title compound as a solid mp >250°. UV: (0.1N HCl) $\lambda_{max}$ 262(22600), 290 sh (4900), 388 (6100) nm; NMR: δ (TFA) 3.69 (s, OCH$_3$); 4.89 (s, OCH$_2$); 8.95 (s, H-7). IR: (KBr) 1725, 1700, 1650, 1605, 1490, 1480, 1390, 1360, 1325, 1235, 1155, 1110, 1065d, 1015d, 970 cm$^{-1}$. Anal. calcd: C, 43.05; H, 4.06; N, 31.38. Found: C, 42.79; H, 4.14; N, 31.21.

3B. (+ −)-2-Amino-5,6,7,8-tetrahydro-6-methoxymethyl-4(3H)-pteridinone. The product from example 3A (1 g) was dissolved in trifluoroacetic acid (10 mL) and at one atmosphere pressure of hydrogen over platinum dioxide catalyst. 6N hydrochloric acid (10 mL) was then added to the reaction mixture which was subsequently filtered to remove the catalyst and evaporated. The crude product was purified by treatment of a solution with activated charcoal and by recrystallization from 6N hydrochloric acid/acetonitrile to give a solid which was dried at approximately 50° C. in vacuo. The analytical and spectroscopic characteristics of the product were identical to those of the compound described in Example 1.

EXAMPLE 4

(+ −)-2-Amino-5,6,7,8-tetrahydro-6-n-butoxymethyl-4(3H)-pteridinone 4A. 2-Amino-3-cyano-5-n-butoxymethylpyrazine-1-oxide. This compound was prepared by reacting 2-amino-3-cyano-5-chloromethylpyrazine-1-oxide with n-butanol under conditions analogous to those described in Example 1. mp 58°-60°. NMR: δ ($d^6$-DMSO) 0.84 (t, 3H); 1.0-1.8 (m, 4H); 3.41 (t, 2H); 4.31 (s, 2H); 7.86 (br s, 2H); 8.37 (s, 1H). Anal. calcd. for $C_{10}H_{14}N_4O_2$: C, 54.04; H, 6.35; N, 25.21. Found: C, 53.96; H, 6.39; N, 25.17.

4B. 2,4-Diamino-6-n-butoxymethylpteridine-8-oxide. The product of Example 4A was reacted with guanidine in methanol according to the procedure described in Example 2 to give the title compound; mp >250°. UV: (0.1N HCl) $\lambda_{max}$ 252.5 (30,900), 282 (10,700), 343.5 (sh) (6,200), 356.5 (8,500), 369.5 (7,800) nm. NMR: δ ($d^6$-DMSO) 0.88 (t, 3H); 1.0-1.8 (m, 4H); 3.51 (t, 2H); 4.49 (s, 2H); 7.01 (br s, 2H); 7.75 (br s, 2H); 8.37 (s, 1H). IR: (KBr) 3700-2800, 1632, 1546, 1461, 1356, 1331, 1163, 1053, 978 cm$^{-1}$. Anal. calcd. for $C_{11}H_{16}N_6O_2$: C, 49.99; H, 6.10; N, 31.80. Found: C, 49.79; H, 6.11; N, 31.67.

4C. 2-Amino-6-n-butoxymethyl-4(3H)-pteridinone-8-oxide. The product of Example 4B was hyrolyzed according to the produce of Example 3A to give the title compound. UV: (0.1N NaOH) $\lambda_{max}$ 261.5, 288 (sh), 390 nm. NMR: δ ($d^6$-DMSO) 0.89 (t, 3H); 1.0-1.8 (m, 4H); 3.48 (t, 2H); 4.45 (s, 2H); 6.25 (br s, 2H); 8.19 (s, *1H).
*ring N-H below δ10.0 was not detected, probably as a result of exchange with the solvent.

4D. (+ −)-2-Amino-5,6,7,8-tetrahydro-6-n-butoxymethyl-4(3H)-pteridinone. The product of Example 4C was treated according to the procedure described in Example 3B to give the title compound, the analytical and spectral details of which are described in Example 2.

EXAMPLE 5

(+ −)-2-Amino-5,6,7,8-tetrahydro-6-ethoxymethyl-4(3H)-pteridinone

The compound was made in a manner similar to that of the 6-methoxymethyl title compound described in Example 1 except the ethoxymethylpyrazine was made by heating the chloromethylpyrazine (VI) in ethanol instead of methanol.

Spectra and microanalytical data of the three intermediates and final product are the following:

5A. 2-Amino-3-cyano-5-ethoxymethylpyrazine. NMR: δ ($d_6$-DMSO) 1.15 (t, 3H); 3.50 (q, 2H); 4.35 (s, 2H); 7.23 (br s, 2H); 8.25 (s, 1H). IR: ($CHCl_3$) ~3400, 2222 (CN), 1611, 1378, 1098 $cm^{-1}$. Anal. calcd. for $C_8H_{10}N_4O$: C, 53.92; H, 5.66; N, 31.44. Found: C, 53.81; N, 5.68; N, 31.41.

5B. 2,4-Diamino-6-ethoxymethylpteridine. mp 247°–248° (dec.). NMR: δ ($d_6$-DMSO) 1.17 (t, 3H); 3.57 (q, 2H); 4.58 (s, 2H); 6.62 (br s, 2H); 7.58 (br s, 2H); 8.73 (s, 1H). IR: (KBr) 3327, 1630, 1440, 1356 $cm^{-1}$. Anal. calcd. for $C_9H_{12}N_6O$: C, 49.08; H, 5.49; N, 38.16. Found: C, 48.81; H, 5.53; N, 38.03.

5C. 2-Amino-6-ethoxymethyl-4(3H)-pteridinone. mp >300°. UV: (0.1N NaOH) (qualitative) $\lambda_{max}$ 254, 277 (sh), 363 nm. NMR: δ ($d_6$-DMSO) 1.14 (t, 3H); 3.54 (q, 2H); 4.55 (s, 2H); 8.66 (br s, 2H); 8.66 (s, 1H); 11.3 (br s, 1H).
IR: (KBr) 1694 (C=O) $cm^{-1}$. Anal. calcd. for $C_9H_{11}N_5O_2 \cdot 0.58\ H_2O$: C, 46.66; H, 5.29; N, 30.23. Found: C, 46.65; H, 4.99; N, 30.27.

5D. (+ −)-2-Amino-5,6,7,8-tetrahydro-6-ethoxymethyl-4(3H)-pteridinone. mp 210.5°–217° (dec.). UV: (0.1N HCl) $\lambda_{max}$ 265.5 (14200) nm. NMR: δ ($d_6$-DMSO) 1.12 (t, 3H); 3.49 (q overlapping m, 7H); 4.0–8.0 (br humps). IR: (KBr) 1660 (C=O) $cm^{-1}$. Anal. calcd. for $C_9H_{15}N_5O_2 \cdot 2HCl \cdot H_2O$: C, 34.18, H, 6.06; N, 22.15; Cl, 22.43. Found: C, 34.29; H, 6.11; N, 22.14; Cl 22.50.

EXAMPLE 6

(+ −)-2-Amino-5,6,7,8-tetrahydro-6-n-propoxymethyl-4(3H)-pteridinone.

This compound was made in a manner similar to that of the 6-methoxymethyl title compound described in Example 1 except that the n-propoxymethylpyrazine was made by heating the chloromethylpyrazine (VI) in n-propanol instead of methanol.

Spectra and microanalytical data of the three intermediates and final product are the following:

6A. 2-Amino-3-cyano-5-n-propoxymethylpyrazine. mp 79°–80.5°. NMR: δ ($d_6$-DMSO) 0.88 (t, 3H); 1.2–1.9 (m, 2H); 3.40 (t, 2H); 4.36 (s, 2H); 7.23 (br s, 2H); 8.25 (s, 1H). Anal. calcd. for $C_9H_{12}N_4O$: C, 56.23; H, 6.29; N, 29.15. Found: C, 56.01; H, 6.30; N, 29.14.

6B. 2,4-Diamino-6-n-propoxymethylpteridine. mp 239°–243° (dec.). NMR: δ ($d_6$-DMSO) 0.89 (t, 3H); 1.57 (sextet, 2H); 3.47 (t, 2H); 4.59 (s, 2H); 4.59 (s, 2H); 6.61 (br s, 2H); 7.57 (br s, 2); 8.73 (s, 1H). IR: (KBr) 3430, 3304, 3132, 1624, 1434, 1353, 1187, 1077, 1064, 813 $cm^{-1}$. Anal. calcd. for $C_{10}H_{14}N_6O$: C, 51.27; H, 6.02; N, 35.88. Found: C, 51.14; H, 6.04; N, 35.85.

6C. 2-Amino-6-n-propoxymethyl-4(3H)-pteridinone. mp >250°; UV: (0.1N NaOH) $\lambda_{max}$ 255 (25000), 276.5 (sh) (6800), 364 (8000) nm. NMR: δ ($d_6$-DMSO) 0.88 (t, 3H); 1.57 (sextet, 2H); 3.47 (t, 2H); 4.58 (s, 2H); 6.90 (br s, 2H); 8.69 (s, 1H); 11.3 (br s, 1H). IR: (KBr) 1693 (C=O) $cm^{-1}$. Anal. calcd. for $C_{10}H_{13}N_5O_2 \cdot 0.20\ H_2O$: C, 50.28; H, 5.66, N, 29.32. Found: C, 50.25; H, 5.63; N, 29.45.

6D. (+ −)-2-Amino-5,6,7,8-tetrahydro-6-n-propoxymethyl-4(3H)-pteridinone. mp 194° (dec.). UV: (0.1N HCl) 265 (15100) nm. NMR: δ ($d_6$-DMSO) 0.88 (t, 3H); 1.56 (sextet, 2H); 2.9–4.0 (m, 7H); 8.2 (br hump). IR: (KBr) 1662 (C=O) $cm^{-1}$. Anal. calcd. for $C_{10}H_{17}N_5O_2 \cdot 2HCl \cdot H_2O$: C, 36.37; H, 6.41; N, 21.21; Cl, 21.47. Found: C, 36.28; H, 6.41; N, 21.18; Cl, 21.46.

EXAMPLE 7

(+ −)-2-Amino-5,6,7,8-tetrahydro-6-isopropoxymethyl-4(3H)-pteridinone

This compound was made in a manner similar to that of the 6-methoxymethyl title compound described in Example 1 except that the isopropoxymethylpyrazine was made by heating the chloromethylpyrazine (VI) in isopropanol instead of methanol.

Spectra and microanalytical data of the three intermediates and the final product are the following:

7A. 2-Amino-3-cyano-5-isopropoxymethylpyrazine. mp 92°–94°. NMR: δ ($d_6$-DMSO) 1.07 (d, 6H); 3.61 (septet, 1H); 4.34 (s, 2H); 7.19 (br s, 2H); 8.25 (s, 1H). Anal. calcd. for $C_9H_{12}N_4O$: C, 56.23; H, 6.29; N, 29.15. Found: C, 56.17; H, 6.30; N, 29.11.

7B. 2,4-Diamino-6-isopropoxymethylpteridine. mp 285°–286° (dec.). NMR: δ ($d_6$-DMSO) 1.16 (d, 6H); 3.73 (septet, 1H); 4.58 (s, 2H); 6.60 (br s, 2H); 7.56 (br s, 2H); 8.73 (s, 1H). IR: (KBr) 3436, 3312, 3146, 2970, 1630, 1559, 1437, 1366, 1194, 1037, 819 $cm^{-1}$. Anal. calcd. for $C_{10}H_{14}N_6O$: C, 51.27; H, 6.02; N, 35.88. Found: C, 51.18; H, 6.06; N, 35.86.

7C. 2-Amino-6-isopropoxymethyl-4(3H)-pteridinone. mp >300°. UV: (0.1N NaOH) $\lambda_{max}$ 254.5 (26000), 275.5 (sh) (7800), 363.5 (8200) nm. NMR: δ ($d_6$-DMSO) 1.18 (d, 6H); 3.74 (septet, 1H); 4.59 (s, 2H); 6.86 (br s, 2H); 8.70 (s, 1H); ~11.3 (br s, 1H). IR: (KBr) 1700 (C=O) $cm^{-1}$. Anal. calcd. for $C_{10}H_{13}N_5O_2$: C, 51.05; H, 5.57; N, 29.77. Found: C, 51.09; H, 5.62; N, 29.71.

7D. (+ −)-2-Amino-5,6,7,8-tetrahydro-6-isopropoxymethyl-4(3H)-pteridinone. mp 210° (dec.). UV: (0.1N HCl $\lambda_{max}$ 265 (14800) nm. NMR: δ ($d_6$-DMSO) 1.12 (d, 6H); 3.2–3.9 (m, 6H); 8.05 (br hump). IR: (KBr) 1669 (C=O) $cm^{-1}$. Anal. calcd. for $C_{10}H_{17}N_5O_2 \cdot 2HCl \cdot H_2O$: C, 36.37; H, 6.41; N, 21.21; Cl, 21.47. Found: C, 36.47; H, 6.42; N, 21.19; Cl, 21.49.

EXAMPLE 8 BIOLOGICAL DATA

Tyrosine hydroxylase was partially purified through a 25–45% ammonium sulfate fraction. Specific activity of this preparation with tetrahydrobiopterin was 4.0 nmole/mg protein (min). The enzyme was assayed by a modification of the method of Nagatsu, T., Levitt, M., and Udenfriend, S. (*Anal. Biochem.* 9, 122, (1964)) where the Dowex chromatography step was replaced by a charcoal extraction.

Tryptophan hydroxylase was assayed according to a modification of the method of Renson J., et al (*Biochem. Biophys. Acta* 25: 504 (1966)). The preparation of tryptophan hydroxylase was a crude 30,000xg supernatant which had been desalted on a Sephadex G-25 (Trade Name) column (Boadle-Biker, M. C., *Biochem Pharmacol.* 28: 2129 (1979). The specific activity of this tryptophan hydroxylase, using $BH_4$ a cofactor, was approximately 100 pmol product per milligram protein per minute at 37°.

Phenylalanine hydroxylase was measured as described by Shiman, R. et al., (*J. Biol. Chem.* 254: 11300 (1979)) except that the product of the reaction (tyrosine) was measured fluorometrically using the method of Waalkes, T. P. and Udenfriend, S. (*J. Lab. Clin. Med.* 50: 733 (1957). Phenylalanine hydroxylase was prepared from rat liver using hydrophobic chromatography (Shiman, R. et al. (*J. Biol. Chem.* 254: 11,300 (1979)). The specific activity of the enzyme, using $BH_4$ as the co-factor, was 1.0 μmol/mg protein per minute at 37°.

Dihydrofolate reductase assay

These assays were carried out on the 7,8-dihydropterin analogs of the compounds of formula I which were tetrahydropterins. The 7,8-dihydropterins were obtained commercially (in the case of dihydrobiopterin) or synthesized from the corresponding compound of formula I. Synthesis of 7,8-dihydropterins involved the combination of 0.27 μmole of a compound of formula I, 20 μg of horseradish peroxidase, 0.6 μmole of hydrogen peroxide in 0.1 ml of 0.5M potassium phosphate buffer, pH 7.5. After 3 min at room temperature, 10 μg of bovine liver catalase was added. The production of the 7,8-dihydropterin was verified by U.V. spectroscopy.

The assay was carried out with bovine liver DHFR using a modification of the method of Bailey and Ayling (*J. Biol. Chem.*, 253, 1598 (1978)) where the desired dihydropterin replaced dihydrobiopterin, and the HPLC system used consisted of an anaerobic 0.1M acetic acid (with or without 10% acetonitrile) solvent on a 25 cm×4.6 mm Dupont TMS-Zorbax column. In our hands, dihydrobiopterin is reduced at a rate 2.5% that of the natural substrate dihydrofolate.

Dihydropteridine reductase was assayed by the method of Craine, et al., (*J. Biol. Chem.*, 247, 6082 (1972)).

TABLE I
BIOPTERIN COFACTOR ANALOGS

| | Compound | |
|---|---|---|
| | 6-Methoxymethyl-tetrahydropterin | Tetrahydrobiopterin |
| Tyrosine hydroxylase | | |
| Km substrate (μM) | 21.9 | 16.0 |
| Km pterin (μM) | 65 | 110 |
| Vmax (%) | 124 | 100 |
| Phenylalanine hydroxylase | | |
| Km substrate (μM) | 111 | 123 |
| Km pterin (μM) | 12.9 | 7.9 |
| Vmax (%) | 79 | 100 |
| Tryptophan hydroxylase | | |
| Km substrate (μM) | 28 | 15 |
| Km pterin (μM) | 103 | 82 |
| Vmax (%) | 54 | 100 |
| | (Quinonoid dihydro) | (Quinonoid dihydro) |
| Dihydropteridine reductase | | |
| Km pterin (μM) | 7 | 1.8 |
| Vmax (%) | 295 | 100 |
| | (7,8-Dihydro) | 7,8-Dihydro |
| Dihydrofolate reductase | | |
| V (%) | 800 | 100 |

EXAMPLE 9: PHARMACEUTICAL FORMULATIONS

9A. Capsule

| Ingredient | Amount per capsule (mg) |
|---|---|
| Compound (Ia) | 325.0 |
| Ascorbic Acid | 174.0 |
| Corn Starch | 100 mg |
| Stearic Acid | 27 mg |

The finely ground active compound was mixed with the powdered excipients lactose, corn starch and stearic acid and packed into gelatin capsule.

9B. Tablet

| Ingredient | Amount per tablet (mg) |
|---|---|
| Compound I | 325.0 |
| Ascorbic Acid | 125.0 |
| Corn Starch | 50.0 |
| Polyvinylpyrrolidone | 3.0 |
| Stearic Acid | 1.0 |
| Magnesium stearate | 1.0 |

The active compound was finely ground and intimately mixed with the powdered excipients lactose, corn starch, polyvinylpyrrolidone, magnesium stearate and stearic acid. The formulation was then compressed to afford one tablet weighing 505 mg.

9C. Suppository

| Ingredient | Amount per suppository |
|---|---|
| Compound (Ia) | 325.0 mg |
| Butylated hydroxy toluene (BHT) | 25 mg |
| Cocoa Butter or Wecobee[+] Base q.s. | 2.0 g |

[+]Wecobee is the trade name of a hydrogenated carboxylic acid.

We claim:
1. The compound of the formula (IIA)

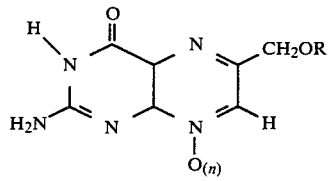

(IIA)

where n is 1 and R represents a lower alkyl of 1 to 8 carbons or a salt thereof.

2. A compound of claim 1 which is 2-amino-6-methoxymethyl-4(3H)-pteridinone-8-oxide.

3. A compound of claim 1 which is 2-amino-6-n-butoxymethyl-4(3H)-pteridinone-8-oxide.

* * * * *